(12) United States Patent
Bayes Genis et al.

(10) Patent No.: US 10,203,341 B2
(45) Date of Patent: Feb. 12, 2019

(54) NEPRILYSIN AS HEART FAILURE PROGNOSTIC MARKER

(71) Applicant: FUNDACIÓ INSTITUT D'INVESTIGACIÓ EN CIÈNCIES DE LA SALUT GERMANS TRIAS I PUJOL, Badalona (ES)

(72) Inventors: Antoni Bayes Genis, Barcelona (ES); Josep Lupón Rosés, Sant Cugat Del Vallès (ES); Amparo Galán Ortega, Barcelona (ES); Jaume Barallat Martínez De Osaba, Barcelona (ES)

(73) Assignee: FUNDACIÓ INSTITUT D'INVESTIGACIÓ EN CIÈNCIES DE LA SALUT GERMANS TRIAS I PUJOL, Badalona (ES)

( * ) Notice: Subject to any disclaimer, the term of this patent is extended or adjusted under 35 U.S.C. 154(b) by 0 days.

(21) Appl. No.: 15/506,665

(22) PCT Filed: Aug. 14, 2015

(86) PCT No.: PCT/EP2015/068729
§ 371 (c)(1),
(2) Date: Feb. 24, 2017

(87) PCT Pub. No.: WO2016/030209
PCT Pub. Date: Mar. 3, 2016

(65) Prior Publication Data
US 2017/0254815 A1    Sep. 7, 2017

(30) Foreign Application Priority Data
Aug. 29, 2014  (EP) .................... 14182846

(51) Int. Cl.
| | | |
|---|---|---|
| *G01N 33/53* | (2006.01) | |
| *G01N 33/573* | (2006.01) | |
| *G01N 33/68* | (2006.01) | |
| *C12Q 1/37* | (2006.01) | |
| *A61P 9/04* | (2006.01) | |
| *C07K 14/47* | (2006.01) | |
| *C07K 16/40* | (2006.01) | |
| *G16H 50/30* | (2018.01) | |

(52) U.S. Cl.
CPC ........... *G01N 33/6893* (2013.01); *C12Q 1/37* (2013.01); *G01N 33/53* (2013.01); *G01N 33/573* (2013.01); *A61P 9/04* (2018.01); *C07K 14/47* (2013.01); *C07K 16/40* (2013.01); *G01N 2333/96497* (2013.01); *G01N 2800/325* (2013.01); *G01N 2800/52* (2013.01); *G16H 50/30* (2018.01)

(58) Field of Classification Search
None
See application file for complete search history.

(56) References Cited

U.S. PATENT DOCUMENTS

2012/0231476 A1    9/2012    Anderberg et al.
2014/0206632 A1    7/2014    Todd et al.

OTHER PUBLICATIONS

Qian et al (2012, J Neurol. 259:2111-2118).*
International Search Report and Written Opinion of the International Searching Authority dated Oct. 20, 2015 for PCT/EP2015/068729, 15 pages.
Bayes-Genis, et al., "Combined Use of High Sensitivity ST2 and NTproBNP to Improve the Prediction of Death in Heart Failure", European Journal of Heart Failure, Jan. 2012; 14:32-8.
Bayes-Genis, et al., "Soluble Neprilysin is Predictive of Cardiovascular Death and Heart Failure Hospitalization in Heart Failure Patients", Journal of the American College of Cardiology, Feb. 2015, vol. 65, No. 7, doi:10.1016/j.jacc.2014.11.048, ISSN 0735-1097, pp. 657-665, XP055175223.
McMurray, et al., "Dual angiotensin receptor and neprilysin inhibition as an alternative to angiotensin-converting enzyme inhibition in patients with chronic systolic heart failure: rationale for and design of the Prospective comparison of ARNI with ACEI to Determine Impact on Global Mortality and morbidity in Heart Failure trial (Paradigm-HF)", European Journal of Heart Failure, Sep. 2013, vol. 15, No. 9, doi:10.1093/eurjhf/hft052, ISSN 1388-9842, pp. 1062-1073, XP055161544.
Standeven, et al., "Neprilysin, obesity and the metabolic syndrome", International Journal of Obesity, Aug. 2011, vol. 35, No. 8, doi:10.1038/ijo.2010.227, ISSN 0307-0565, pp. 1031-1040, XP055175907.
Stasch, et al., "Renal and antihypertensive effects of neutral endopeptidase inhibition in transgenic rats with an extra renin gene", American Journal of Hypertension, Aug. 1996, vol. 9, No. 8, pp. 795-802, XP055175808.
Wegner, et al., "Role of neutral endopeptidase 24.11 in AV fistular rat model of heart failure", Cardiovascular Research, Jun. 1996, vol. 31, No. 6, doi:10.1016/0008-6363(96)00062-4, ISSN 0008-6363, pp. 891-898, XP055175803.

* cited by examiner

*Primary Examiner* — Zachary C Howard
(74) *Attorney, Agent, or Firm* — Squire Patton Boggs (US) LLP

(57) ABSTRACT

The present invention provides an in vitro method for determining the prognosis in a patient suffering a heart failure disease, the method comprising the step of determining the level of soluble neprilysin (NEP) in a test sample of the patient.

13 Claims, 1 Drawing Sheet
Specification includes a Sequence Listing.

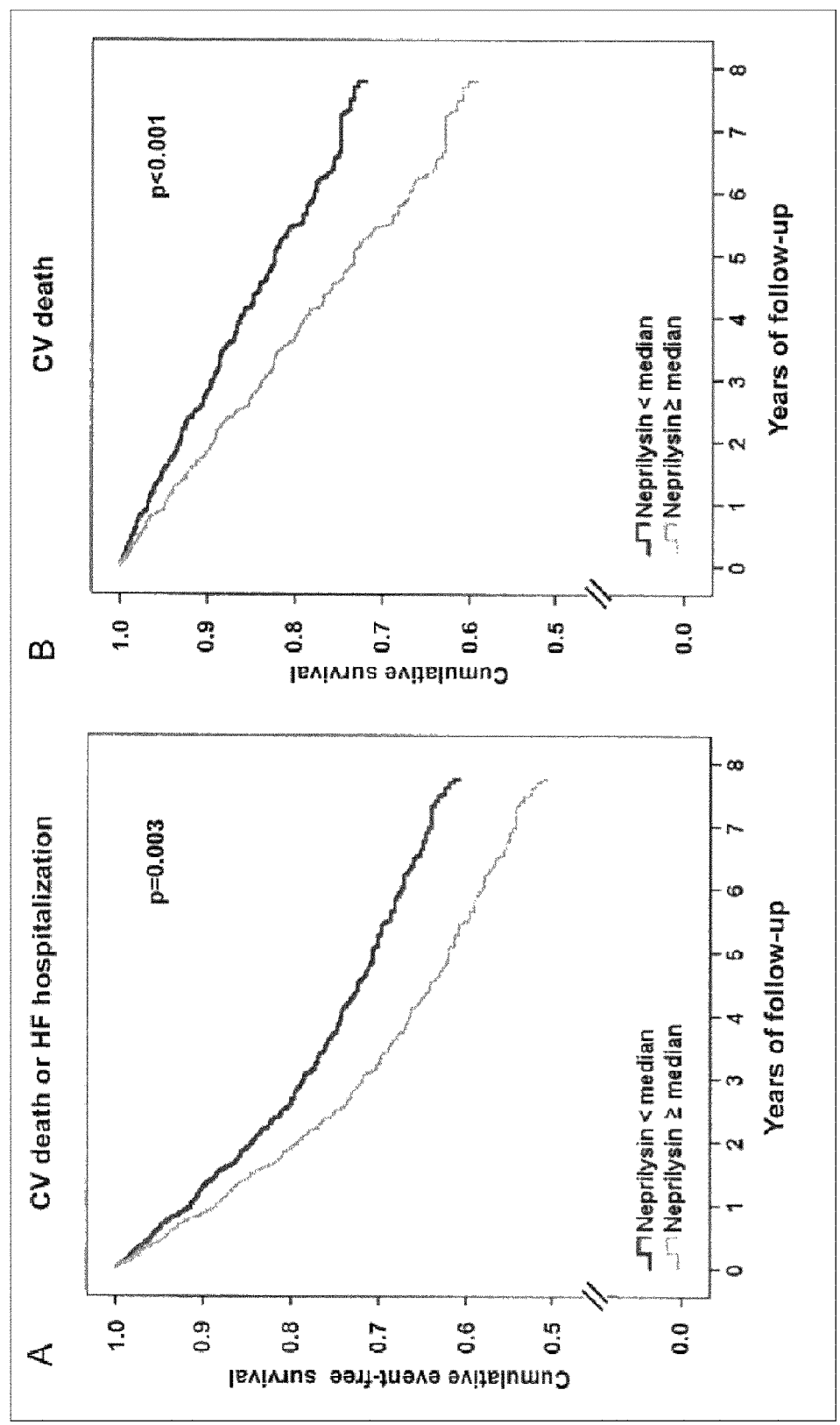

NEPRILYSIN AS HEART FAILURE PROGNOSTIC MARKER

The present invention is in the field of clinical prognosis. Particularly the present invention relates to the prognosis of adverse events (such as cardiovascular mortality) in patients with heart failure (HF).

BACKGROUND ART

Heart failure (HF), also termed congestive HF (CHF) is a cardiac condition that occurs when a problem with the structure or function of the heart impairs its ability to supply sufficient blood flow to meet the body's needs. It can cause a large variety of symptoms, particularly shortness of breath (SOB) at rest or during exertion and/or fatigue, signs of fluid retention such as pulmonary congestion or ankle swelling, and objective evidence of an abnormality of the structure or function of the heart at rest. However, some patients can be completely symptom free and asymptomatic structural or functional abnormalities of the heart are considered as precursors of symptomatic heart failure and are associated with high mortality.

Heart failure is a common disease: more than 2% of the U.S. population, or almost 5 million people, are affected and 30 to 40% of patients die from heart failure within 1 year after receiving the diagnosis.

Heart failure is often undiagnosed due to a lack of a universally agreed definition and challenges in definitive diagnosis, particularly in the early stage.

With appropriate therapy, heart failure can be managed in the majority of patients, but it is a potentially life threatening condition, and progressive disease is associated with an overall annual mortality rate of 10%. In addition, it is the leading cause of hospitalization in people older than 65 years. As a consequence, the management of heart failure consumes 1-2% of total health-care expenditure in European countries.

Chronic HF is a long-term condition developing over months and years with a usually stable treated symptomatology. This condition is associated with heart undergoing adaptive responses that, however, can be deleterious in the long-term and lead to a worsening condition. Acute HF (AHF) is a term used to describe exacerbated or decompensated heart failure, referring to episodes in which a patient can be characterized as having a change in heart failure signs and symptoms resulting in a need for urgent therapy or hospitalization. AHF develops rapidly during hours or days and can be immediately life threatening because the heart does not have time to undergo compensatory adaptations. Chronic HF may also decompensate which most commonly result from an intercurrent illness (such as pneumonia), myocardial infarction, arrhythmias, uncontrolled hypertension, or a patient's failure to maintain a fluid restriction, diet or medication.

The possibility of predicting adverse events at presentation of the patient is important, since early recognition of risk is a prerequisite for initiating measures helping to prevent the development of adverse events. In this regard, several attempts have been made in order to find markers that can provide accurate prognostic information.

Clinically, several biomarkers have received great attention as predictors of prognosis in HF, being natriuretic peptides the most extensively used, but others, such as ST2 and high-sensitivity troponin T, have also shown promising results, doing so in an additive fashion to natriuretic peptides. When measuring the level of the biomarker, it is also very important that clinicians understand confounding factors that may weaken or undermine the accuracy of the test. A classic example of this is how body-mass index or impaired renal function influences blood concentrations of natriuretic peptides in HF.

Therefore, in spite of the efforts made, there is still the need of further prognostic markers which can provide useful information in the managing of HF disease.

SUMMARY OF THE INVENTION

The present inventors have found circulating soluble neprilysin (hereinafter also referred as "NEP") levels in samples of patients suffering from HF. In particular, circulating levels of soluble NEP in serum of patients with chronic HF have been extensively detected. In addition, as it is illustrated below, it has been found a positive association of NEP with cardiovascular outcomes.

NEP, as explained in detail below, is a membrane bound enzyme with a large extracellular catalytic domain, a single transmembrane region and a short (27 amino acids) cytoplasmic N-terminal domain. This enzyme has been disclosed in the state of the art as diagnostic or prognostic marker in several types of cancer or renal diseases.

Surprisingly, the present inventors have found that this enzyme can be useful as a prognostic marker of HF.

On the other hand, some previous reports have identified the presence of NEP in biological fluids. However, no evidence exists of circulating soluble NEP as a pathobiological surrogate in patients with HF.

Thus, in a first aspect the present invention provides an in vitro method for determining the prognosis in a patient suffering a heart failure disease, the method comprising the step of determining the level of soluble neprilysin (NEP) in a test sample of the patient.

As it is explained in detail below, a large real-life consecutive cohort of 1069 patients was followed for a mean 4.1 years with 335 composite endpoint events, and it was found that NEP was a good pathobiological surrogate of CV mortality and morbidity, even after adjustment in a very comprehensive multivariable model that included 12 prognostically meaningful variables including NT-proBNP, which is one of the more widely used biomarker in HF prognosis. As shown in Table 2, wherein the results of the multivariate analysis are summarized, the prognostic information provided by NEP is significant (because the p value is lower than 0.05) and it is independent from other parameters taken into account during such analysis. The skilled person in the art knows that when multivariate analysis are performed, biomarkers which, at a first sight, seem to be adequate for the diagnosis or prognosis of a disease, at the end are disregarded because they are statistically negatively interfered by other biomarkers or by considering other parameters (such as age or sex, among others). Table 3 below, which is another multivariant statistical analysis, illustrates that the prognostic information provided by soluble NEP is not affected when other prognostic HF markers, ST2 and high-sensitivity troponin T, are included in the analysis, contrary to NTproBNP, which loses its statistical significance.

From data of Tables 2 and 3, therefore, it can be concluded that soluble NEP provides prognostic information independently of the parameters and other biomarkers considered in the assay. And, consequently, the data provided below support the great value of NEP as prognostic tool of patients with HF.

In a second aspect, the present invention provides the use of soluble NEP as prognostic marker of HF.

In a third aspect, the present invention provides the use of means for detecting the presence of soluble NEP in an isolated sample for the prognosis of heart failure disease in the method as defined in the first aspect of the invention.

In a fourth aspect, the present invention provides a method of deciding or recommending whether to initiate a medical regimen based on NEP inhibitors, which method comprises the steps of (a) determining, in vitro, the amount of soluble NEP in a test sample of the patient; and (b) comparing the level obtained in step (a) with a reference value, wherein if the amount of soluble NEP detected in step (a) is higher than the reference value it is indicative that the patient would benefit from a medical regimen based on NEP inhibitors.

Determining the soluble NEP level in a test sample, the skilled person can establish, additionally, which is the most suitable therapy that can be recommended, because the level detected in the sample may reflect the extension (i.e., severity) of the syndrome. The higher the level of soluble NEP is determined in the test sample, the more beneficial the administration of NEP inhibitors to the HF patient can be.

Furthermore, once it has decided to initiate the medical regimen because the subject is suffering from HF syndrome (following the method defined in the second aspect of the invention), it can be monitored how efficient is the regimen: a decrease or return to a normal level of soluble NEP can indicate that the HF patient has reacted favorably to the medical regimen and, therefore, said regimen is effective; if the level of soluble NEP does not significantly change or it increases, this can indicate that the medical regimen is not effective.

BRIEF DESCRIPTION OF THE DRAWINGS

FIG. 1 represents an age-adjusted Cox regression curves. A—event-free survival curve for the primary composite end-point of CV death or HF hospitalization. B—survival curve for CV death. Median value of NEP=0.642 ng/mL. Black line=neprilysin<median; grey line=neprilysin median.

DETAILED DESCRIPTION OF THE INVENTION

As it has been stated above, the present invention provides a method for determining the prognosis in a patient suffering from HF.

"Prognosis" relates to the prediction of an adverse event (e.g. mortality) for a patient with heart failure. This may include an estimation of the chance of recovery or the chance of death for said patient. "Adverse event" is defined as worsening or decompensation of heart failure, and mortality. "Mortality" is defined as cardiovascular death (attributable to e.g. myocardial ischemia and infarction, heart failure, cardiac arrest or cerebrovascular accident) and non-cardiovascular mortality (including all other causes of death, e.g. infection, malignancies). So, in one embodiment, the "bad prognosis" is selected from the group consisting of: worsening or decompensation of heart failure, and cardiovascular mortality. In another embodiment, the bad prognosis is the risk of mortality.

HF, also termed CHF is a cardiac condition that occurs when a problem with the structure or function of the heart impairs its ability to supply sufficient blood flow to meet the body's needs.

In one embodiment, the patient suffers chronic HF.

"Chronic HF" is a long-term condition (months/years) usually with stable treated symptomatology, that is associated with the heart undergoing adaptive responses (e.g. dilation, hypertrophy) to a precipitating cause. These adaptive responses, however, can be deleterious in the long-term and lead to a worsening condition. Patients with chronic HF can be grouped into stable, worsening and decompensated chronic HF patients. Decompensation in chronic HF patients most commonly result from an intercurrent illness (such as pneumonia), myocardial infarction, arrhythmias, uncontrolled hypertension, or a patient's failure to maintain a fluid restriction, diet or medication. Chronic HF, which is worsening or decompensated, is characterized as having a change in HF signs and symptoms resulting in a need for urgent therapy or therapy adjustment and the requirement of hospitalization.

Common factors that precipitate hospitalization for heart failure are e.g. acute myocardial ischemia, noncompliance with the medical regimen (sodium and/or fluid restriction), uncorrected high blood pressure, atrial fibrillation and other arrhythmias, pulmonary embolus or concurrent infections.

Neprilysin (NEP) is a membrane bound enzyme with a large extracellular catalytic domain, a single transmembrane region and a short (27 amino acids) cytoplasmic N-terminal domain. Its sequence is available in Uniprot database (version 180, last modified Jul. 9, 2014) with the reference code P08473. This enzyme catalyzes the degradation of a number of vasodilator peptides, including natriuretic peptides, and also contributes to the breakdown of angiotensin II.

The soluble form of NEP, which is the one detected in the method of the present invention, is the form of NEP not bound to membrane. In one embodiment the soluble NEP form differs from the wild-type with reference code P08473 in that it lacks the transmembrane and intracellular domain, and corresponds to sequence SEQ ID NO: 1.

The term "patient" as used herein refers to a living human or non-human organism that is receiving medical care or that should receive medical care due to a disease. This includes persons with no defined illness who are being investigated for signs of pathology. Thus the methods and assays described herein are applicable to both, human and veterinary disease.

In one embodiment of the first aspect of the invention, when the level of soluble NEP is higher than a reference value it is indicative of bad prognosis.

As it can be derived from the results shown below, the risk of suffering an adverse event increases, proportionally, with increasing levels of NEP. For one standard deviation of NEP logarithmic transformation, the risk of suffering an adverse event increases about 18%.

The term "reference value" referred to in the method of the first aspect is to be understood as a predefined value of molecular marker soluble NEP, which is derived from the levels of said molecular marker in a sample or group of samples. The samples are taken from a subject or group of subjects which has/have not still shown any adverse outcome. The skilled person in the art, making use of the general knowledge, is able to choose the subject or group of subjects more adequate for obtaining the reference value.

In one embodiment, the reference value is determined from a population of patients suffering HF In such circumstances, if it was found that soluble NEP level was increased when compared to the reference value, it would be indicative that the patient is getting worse. And, from said data, the clinician is able to take appropriate decisions to treat the patient and keep him alive.

In another embodiment, when the patient suffering HF is being routinely monitored by the clinician, the "reference value" can correspond to the soluble NEP level one at the beginning of the monitoring of the patient or to the one determined in the last health check. Or alternatively, the reference value can be determined from the population of patients suffering HF that have not shown any adverse outcome yet, as stated above. In this way, if it is found an increase in the level of soluble NEP, it would be indicative that the patient is getting worse, and that it is likely that an adverse outcome occurred. This information will allow the clinician to optimize the treatment of the patient.

Methods for obtaining the reference value from the group of selected subjects are well-known in the state of the art.

For instance, in the examples below, the reference value, 0.642 ng/mL, corresponds to the median of the soluble NEP levels determined from a population of HF patients in an ambulatory setting It could be determined that HF patients with soluble NEP levels higher than said reference value had a risk of adverse event increased by 37%.

In an embodiment of the invention the sample is selected from the group consisting of blood, serum, plasma, urine, and cerebrospinal fluid. In another embodiment, the sample is blood, plasma or serum. In still another embodiment, the sample is serum.

In another embodiment of the method of the first aspect of the invention, it is determined the concentration of soluble NEP.

In one embodiment, the level of soluble NEP is determined by an immunoassay technique.

An "immunoassay" is a biochemical test that measures the presence or concentration of a macromolecule in a solution through the use of an antibody, immunoglobulin, or a fragment thereof. Immunoassays come in many different formats and variations. Immunoassays may be run in multiple steps with reagents being added and washed away or separated at different points in the assay. Multi-step assays are often called separation immunoassays or heterogeneous immunoassays. Some immunoassays can be carried out simply by mixing the reagents and sample and making a physical measurement. Such assays are called homogenous immunoassays or less frequently non-separation immunoassays. The use of a calibrator is often employed in immunoassays. Calibrators are solutions that are known to contain the analyte in question, and the concentration of that analyte is generally known. Comparison of an assay's response to a real sample against the assay's response produced by the calibrators makes it possible to interpret the signal strength in terms of the presence or concentration of analyte in the sample.

Advantageously, determining the concentration of protein it is determined the total amount of NEP in sample, independently of whether it is active or not, thus obtaining more accurate information about the real soluble NEP level circulating in the body fluid, with the consequent advantages for the appropriate prognostic of the disease.

Advantageously, immunoassays overcome some of the drawbacks shown by the enzymatic methods, such as the susceptibility due to the substrate as well as to the fact that the catalytic site of the enzyme can be altered during the different stages of the disease.

Immunoassays can generally be classified as: competitive, homogeneous immunoassays; competitive, heterogeneous immunoassays; one-site, noncompetitive immunoassays; and two-site, noncompetitive immunoassays.

In one embodiment, the immunoassay is a competitive, homogeneous immunoassay. In another embodiment the immunoassay is an ELISA.

There are available in the market several ELISA kits for determining the concentration of soluble NEP, such as those marketed by R&D Systems, Raybiotech or Aviscera Bioscience, among others.

In one embodiment, when the ELISA analysis is performed, the sample is diluted before incubation from 1/10 to 1/2. In another embodiment, the sample is diluted before incubation 1/4.

In another embodiment, when the ELISA is performed, the incubation step is performed at a constant temperature selected from the temperature range comprised from 25 to 37° C., with 1000 rpm mixing. In another embodiment the constant temperature of the incubation step is 30° C.

In another embodiment the incubation step, when performing the ELISA, is comprised from 120 to 180 h. In another embodiment the incubation step is of 150 minutes.

In still another embodiment, the ELISA detection is performed: (a) diluting ¼ the serum sample before incubation; and incubating the mixture for 150 minutes at 30° C. at 1000 rpm. Under such conditions the inventors have found that an improvement in the sensitivity is achieved.

In a third aspect, the present invention provides the use of means for performing any one of the method of the first aspect of the invention.

In the present invention, the term "antibody or a fragment thereof with the ability of binding to soluble NEP" is to be understood as any immunoglobulin or fragment thereof able to bind the antigen defined by soluble NEP. It includes monoclonal and polyclonal antibodies. The term "fragment thereof" encompasses any part of an antibody having the size and conformation suitable to bind an epitope of NEP. Suitable fragments include F(ab), F(ab') and Fv. An "epitope" is the part of the antigen being recognized by the immune system (B-cells, T-cells or antibodies).

There are well known means in the state of the art to prepare and characterise antibodies. The methods to generate polyclonal antibodies are well known in the state of the art. Briefly, a polyclonal antibody is prepared by immunising an animal with an immunogenic composition and collecting serum from the immunised animal. A wide range of animal species can be used to produce the antiserum. The animals typically used to produce antiserum can be rabbits, mice, rats, hamsters, guinea pigs or goats.

On the other hand, monoclonal antibodies (MAbs) can be easily prepared using well-known techniques. The procedures for preparing monoclonal antibodies are generally started along the same lines as the preparation of polyclonal antibodies. Animals are injected the antigen as indicated above. The antigen can be mixed with adjuvants, such as Freund's complete or incomplete adjuvant. Vaccination with the same antigen is repeated approximately every two weeks. After immunisation, somatic cells with potential for antibody production are chosen, specifically B lymphocytes (B cells), for use in the protocol for MAb generation. These cells can be obtained from biopsied spleen, lymph nodes or tonsils, or from peripheral blood samples. Antibody-producing B lymphocytes from the immunised animal are then fused with cells from cells from a line of immortal myeloma cells, generally from the same species as the immunised animal. Myeloma cell lines that are adequate for use in fusion procedures for the production of hybridomas are preferably not antibody-producing cells, but have high fusion efficacy and enzyme deficiencies that therefore make them unable to grow in certain culture mediums that only support the growth of the desired fused cells (hybridomas).

In one embodiment, soluble NEP is detected using a policlonal antibody, such as those provided by USCN Life Sciences Inc; LifeSpan Biosciences or RayBiotech, among others.

In one embodiment, the means is an antibody or a fragment thereof which specifically binds to soluble NEP.

In yet another embodiment, the means forms part of a kit.

The kit may additionally comprise further means (additives, solvents) to visualize the interactions (dipsticks, chemiluminescent reagents, turbidimetric reagents, etc.). Suitable additives, solvents and reagents to visualize the antigen-antibody interaction are disclosed in the examples.

The in vitro method of the invention provides prognostic information. In one embodiment, the prognostic information can be collected in a suitable data carrier. Examples of suitable data carrier are paper, CDs, USB, computer archives in PCs, or sound registration with the same information.

Finally, in a fourth aspect the present invention provides a method of deciding or recommending whether to initiate a medical regimen based on NEP inhibitors of a patient suffering HF.

In one embodiment of the fourth aspect of the invention, the subject is a patient suffering HF.

In another embodiment of the fourth aspect of the invention, the subject is a patient suffering HF and the higher levels of soluble NEP, when compared to the reference value is indicative of bad prognosis.

Illustrative non-limitative examples of NEP inhibitors are AHU-377, a component of LCZ696, Omapatrilat; RB-101; and UK-414.495.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

1. Methods
Study Population

From May 2006 to May 2013, ambulatory patients treated at a multidisciplinary HF clinic were consecutively included in the study. Referral inclusion criteria and blood sample obtaining were made as described by Bayes-Genis A. et al. (Bayes-Genis A. et al., 2012). In summary, patients were referred to the HF clinic by cardiology or internal medicine departments and, to a lesser extent, from the emergency or other hospital departments. The principal referral criterion was HF according to the European Society of Cardiology guidelines irrespective of etiology, at least one HF hospitalization, or a reduced left ventricular ejection fraction (LVEF). NEP and NT-proBNP were analyzed from the same blood sample stored at −80°, without previous freeze-thaw cycles. All samples were obtained between 09:00 am to 12:00 pm.

All participants provided written informed consent, and the local ethics committee approved the study. All study procedures were in accord with the ethical standards outlined in the Helsinki Declaration of 1975, as revised in 1983.
Follow-Up and Outcomes All patients were followed at regular predefined intervals, with additional visits as required in case of decompensation. The regular visitation schedule included a minimum of quarterly visits with nurses, biannual visits with physicians, and elective visits with geriatricians, psychiatrists, and rehabilitation physicians. Patients who did not attend the regular visits were contacted by telephone.

The primary outcome was the composite of cardiovascular (CV) death or HF hospitalization. CV and all-cause death were also explored as secondary outcomes. A death was considered from CV origin if it was caused by: heart failure (decompensated heart failure or treatment-resistant heart failure, in the absence of another cause); sudden death (unexpected death, witnessed or not, of a previously stable patient with no evidence of worsening heart failure or any other cause of death); acute myocardial infarction (AMI) (directly related in time with AMI, whether due to mechanic, hemodynamic or arrhythmic complications); stroke (associated with recently appearing acute neurologic deficit); procedural (post-diagnostic or post-therapeutic procedure death); and other cardiovascular causes (eg, rupture of an aneurysm, peripheral ischemia, or aortic dissection). Hospitalizations were identified from HF clinic records, other hospital wards and from the electronic Catalan history record. Fatal events were identified from HF clinic records, other hospital wards, the emergency room, general practitioners, and by contacting the patient's relatives. Furthermore, data was verified from databases of the Catalan and Spanish Health Systems.
Neprilysin Assay Human NEP was measured using a modified sandwich immunoassay (HUMAN NEP/CD10 ELISA KIT, Aviscera Biosciences, Santa Clara, USA, Ref. SK00724-01, Lot No. 20111893). To improve analytical sensitivity of the method and to obtain a lower limit of sample quantification several modifications were made: a) serum aliquots were diluted ¼ in dilution buffer provided by the manufacturer (DB09) before incubation; b) the kit was transferred to an automated robotic platform (Basic Radim Immunoassay Operator 2 [BRIO 2], Radim spa, Pomezia, Italy) performing all incubations at a constant 30° C. temperature, with 1000 rpm mixing; and c) initial sample incubation was extended to 150 minutes, thus achieving a higher slope in the calibration curve and better assay sensitivity. The modified protocol displayed an analytical measurement range from 0.250 to 16 ng/mL. Intra- and inter-assay coefficients of variation were of 3.7% and 8.9%, respectively.
NT-ProBNP Assay NT-proBNP levels were determined from serum using an immuno-electro-chemiluminescence assay on the Modular Analytics E 170 (Roche Diagnostics). This assay has <0.001% cross-reactivity with bioactive BNP, and in the constituent studies in this report, the assay had inter-run coefficients of variation ranging from 0.9% to 5.5%.
hs-cTnT Assay Troponin levels were measured from serum samples by electrochemiluminescence immunoassay using an hs-cTnT assay on the Modular Analytics E 170 (Roche Diagnostics) using manufacturer's instructions. The hs-cTnT assay had an analytic range from 3 to 10,000 ng/L. At the 99th percentile value of 13 ng/L, the coefficient of variation was 9%. The analytic performance of this assay has been validated and complies with the recommendations of the Task Force for use in the diagnosis of myocardial necrosis.

hs-ST2 Assay

ST2 was measured from serum samples using a high-sensitivity sandwich monoclonal immunoassay (Presage™ sST2 assay, Critical Diagnostics, San Diego, Calif., USA)) following manufacturer's instructions. The hs-ST2 assay had a within-run coefficient of <2.5% and total coefficient of variation of 4%.

Statistical Analysis

Categorical variables were expressed as percentages. Continuous variables were expressed as the mean±standard deviation or median (Q1-Q3) according to normal or non-normal distribution. Normal distribution was assessed with normal Q-Q plots. Correlation between NEP levels and age, left ventricular ejection fraction (LVEF), NT-proBNP and estimated glomerular filtration rate (CKD-EPI) were analyzed using the rho Spearman coefficient. Differences in NEP concentrations among sex and etiology groups were assessed with the Mann-Whitney U test. Statistical differences (P-value for trend) in NEP levels for New York Heart Association (NYHA) functional class groups were computed using Spearman test. Age-adjusted Cox regression analyses were performed and survival curves were plotted for the composite primary end-point and for CV mortality relative to NEP median values.

Multivariable survival analyses were also performed using Cox regression models. NEP values were log-transformed and 1 SD was used for hazard ratio (HR) calculation. The following variables were incorporated into the model: age, sex, ischemic etiology of HF, LVEF, NYHA functional class, presence of diabetes mellitus, hemoglobin (g/dL), serum sodium (mmol/L), estimated glomerular filtration rate, NT-proBNP, β-blocker treatment, angiotensin-converting enzyme inhibitor (ACEI) or angiotensin II receptor blocker (ARB) treatment, and NEP. Statistical analyses were performed using SPSS 15 (SPSS Inc., Chicago, Ill.). A two-sided P<0.05 was considered significant.

Results

Circulating soluble NEP was measured in 1069 HF patients attended consecutively from May 2006 to May 2013. Table 1 shows the baseline characteristics of the entire sample and of the subgroup of patients that fulfilled the PARADIGM-HF study inclusion criteria (NYHA class II-IV, LVEF ≤35%, NTproBNP ≥600 ng/L or NTproBNP ≥400 ng/L if HF admission in previous year, treated with ACEI or ARB and with β-blockers unless contraindicated or not tolerated; PARADIGM-like cohort, N=480). During a mean follow-up period of 4.1±2.4 years 449 patients died, 247 from CV causes, 169 from non-CV causes (37.6%) and 33 of unknown cause (7.3%). Among known CV causes of death, refractory HF was responsible in 128 (51.8%) patients, sudden death in 53 (21.4%) patients, and acute myocardial infarction in 23 (9.3%) patients. 235 patients were admitted for HF hospitalization during follow-up, and 335 patients fulfilled the primary endpoint of CV death or HF hospitalization. Five patients were lost to follow-up and adequately censored.

Circulating Soluble NEP

Median soluble NEP levels were 0.642 ng/ml (Q1-Q3 0.385-1.219 ng/mL). One-hundred and fifty-six patients (14.6%) had NEP levels below the analytical measurement range. NEP levels modestly but significantly correlated with age (rho 0.16, p<0.001); in contrast, no correlations were found between NET and LVEF (rho 0.02, p=0.35), estimated glomerular filtration rate (rho 0.05, p=0.1), NTproBNP (rho=−0.01, p=0.68), or NYHA functional class (p for trend 0.72). NEP levels were no gender different (p=0.28) but were significantly higher in non-ischemic vs. ischemic patients (0.690 ng/ml [0.450-1.401] vs. 0.611 ng/ml [0.328-1.046], respectively; p=0.002).

NEP and Outcomes

Age-adjusted NEP values relative to the median were significantly associated with the composite primary endpoint of CV death or HF hospitalization (HR 1.37 [95% CI 1.11-1.69], p=0.003), CV death (HR 1.60 [95% CI 1.24-2.06], p<0.001) and all-cause death (HR 1.27 [95% CI 1.06-1.53], p=0.01). FIG. 1 illustrates the diverging survival curves for the composite end-point and for CV death relative to NEP median values.

As a continuous variable, age-adjusted NEP was also significantly associated with the composite primary endpoint of CV death or HF hospitalization (HR 1.17 [95% CI 1.06-1.29], p=0.001), and CV death (HR 1.19 [95% CI 1.06-1.32], p=0.002); with a trend towards significance in all-cause death (HR 1.09 [95% CI 1.00-1.19], p=0.06). In a comprehensive multivariable analysis including NT-proBNP, soluble NEP remained significantly associated with the composite primary endpoint (HR 1.18 [95% CI 1.07-1.31], p=0.001) and CV mortality (HR 1.18 [95% CI 1.05-1.32], p=0.006) (Table 2).

A PARADIGM-like cohort out of this real-life HF series was also examined, and circulating NEP levels remained significantly associated with the composite primary endpoint of CV death or HF hospitalization in the comprehensive multivariable analysis (HR 1.23 [95% CI 1.05-1.43], p=0.008).

In conclusion, HF is a clinical disease characterized by upregulation of multiple neurohormonal pathways, including the renin-agiotensin-aldosterone system and natriuretic peptides. Within the natriuretic peptide axis NEP is a crucial enzyme. The present inventors have demonstrated for the first time that high levels of NEP are found in the circulation of patients with HF, and that NEP concentrations are indicators of adverse outcomes, both CV mortality and morbidity.

In addition, the reported data is indicative that NEP inhibition, already present in the ARNi LCZ696, is necessary for targeting novel pathophysiological contributors to HF and is crucial for improving patient outcomes.

TABLE 1

|  | Total Cohort<br>N = 1069 | PARADIGM-like<br>N = 480 |
|---|---|---|
| Age, yr* | 66.2 ± 12.8 | 67.5 ± 11.5 |
| Male - no. (%) | 768 (71.8) | 371 (77.3) |
| White - no. (%) | 1061 (99.3) | 476 (99.2) |
| Etiology - no. (%) |  |  |
| Ischemic heart disease | 545 (51) | 288 (60.0) |
| Dilated cardiomyopathy | 123 (11.5) | 64 (13.3) |
| Hypertensive | 97 (9.1) | 26 (5.4) |
| Etoh | 58 (5.4) | 26 (5.4) |
| Toxic (drugs) | 31 (2.9) | 12 (2.5) |

TABLE 1-continued

|  | Total Cohort N = 1069 | PARADIGM-like N = 480 |
|---|---|---|
| Valvulat | 117 (10.8) | 33 (6.9) |
| Other | 98 (9.3) | 31 (6.5) |
| HF duration, months* | 24 (3-70) | 20 (2-72) |
| LVEF, in %* | 33.5 ± 13.3 | 26.01 ± 6.4 |
| NYHA functional class - no. (%) | | |
| I | 62 (5.8) | 0 (0) |
| II | 746 (69.8) | 362 (75.4) |
| III | 254 (23.7) | 115 (24) |
| IV | 7 (0.7) | 3 (0.6) |
| Sodium mmol/L* | 138.7 ± 5.7 | 138.5 ± 3.5 |
| Hemogloblin, g/dl* | 12.9 ± 1.9 | 13.0 ± 1.8 |
| eGFR, ml/min/1.73 m$^2$* | 55.2 ± 26.6 | 54.2 ± 25.2 |
| NT-proBNP ng/L*‡ | 1302 (531-2935) | 1824 (971-3829) |
| Neprilysin, ng/mL† | 0.642 (0.385-1.219) | 0.637 (0.389-1.220) |
| Hypertension, no. (%) | 668 (62.5) | 292 (60.8) |
| Diabetes mellitus, no. (%) | 385 (36.0) | 188 (39.2) |
| Treatment (follow-up), no. (%) | | |
| ACEI or ARB | 952 (89.1) | 480 (100) |
| β-blocker | 964 (90.2) | 447 (93.1) |
| MRA | 623 (58.3) | 336 (70) |
| Loop diuretic | 970 (90.7) | 447 (93.1) |
| Digoxin | 413 (38.6) | 197 (41) |

*Mean ± standard deviation;
†Median (Q1-Q3);
‡NTproBNP available in 1030 patients.
ACEI, angiotensin-converting enzyme inhibitor;
ARB, angiotensin II receptor blocker;
eGFR, estimated glomerular filtration rate (CKD-EPI);
Etoh, alcoholic cardiomyopathy;
HF, heart failure;
LVEF, left ventricular ejection fraction;
MRA: Mineralcorticoid Receptor Antagonist;
NT-proBNP, N-terminal pro-brain natriuretic peptide;
NYHA, New York Heart Association.

TABLE 2

Multivariable Cox regression analysis for risk of composite primary endpoint and CV death.

|  | Composite primary endpoint | | | Cardiovascular death | | |
|---|---|---|---|---|---|---|
|  | HR | 95% CI | P value | HR | 95% CI | P value |
| Age | 1.03 | 1.02-1.04 | <0.001 | 1.04 | 1.02-1.05 | <0.001 |
| Female | 0.74 | 0.58-0.95 | <0.001 | 0.63 | 0.46-0.86 | 0.003 |
| Ischemic etiology of HF | 1.09 | 0.89-1.38 | 0.50 | 1.06 | 0.80-1.40 | 0.71 |
| LVEF | 1.01 | 1.00-1.02 | 0.08 | 1.01 | 1.00-1.02 | 0.21 |
| NYHA functional class | 1.61 | 1.31-1.98 | <0.001 | 1.75 | 1.37-2.22 | <0.001 |
| eGFR, ml/min/1.73 m$^2$ | 0.99 | 0.98-1.00 | 0.002 | 0.99 | 0.99-1.00 | 0.004 |
| Diabetes mellitus | 1.42 | 1.14-1.77 | 0.002 | 1.42 | 1.09-1.85 | 0.009 |
| ACEI or ARB treatment | 0.87 | 0.62-1.21 | 0.40 | 0.70 | 0.48-1.03 | 0.07 |
| β-blocker treatment | 0.54 | 0.39-0.76 | <0.001 | 0.44 | 0.30-0.65 | <0.001 |
| Sodium | 0.99 | 0.98-1.01 | 0.37 | 0.99 | 0.97-1.00 | 0.10 |
| Hemoglobin | 0.93 | 0.87-0.99 | 0.03 | 0.97 | 0.90-1.05 | 0.44 |
| NT-proBNP* | 1.32 | 1.15-1.51 | <0.001 | 1.43 | 1.21-1.69 | <0.001 |
| Neprilysin* | 1.18 | 1.07-1.31 | 0.001 | 1.18 | 1.05-1.32 | 0.006 |

TABLE 3

Multivariable Cox Regression Analysis (backward stepwise) including other biomarkers (NT-proBNP, hs-cTnT and ST2) for Risk of Composite Primary Endpint and CV Death.

|  | Composite Primary Endpoint | | | Cardiovascular Death | | |
|---|---|---|---|---|---|---|
|  | HR | 95% CI | P value | HR | 95% CI | P value |
| Age | 1.03 | 1.02 to 1.04 | <0.001 | 1.03 | 1.02 to 1.05 | <0.001 |
| Female | 0.84 | 0.64 to 1.10 | 0.21 | 0.75 | 0.54 to 1.04 | 0.09 |
| Ischemic etiology of HF | 1.01 | 0.78 to 1.29 | 0.97 | 0.96 | 0.71 to 1.29 | 0.78 |
| LVEF | 1.01 | 1.00 to 1.02 | 0.10 | 1.01 | 1.00 to 1.02 | 0.02 |
| NYHA functional class | 1.48 | 1.18 to 1.96 | 0.001 | 1.58 | 1.20 to 2.03 | 0.001 |
| eGFR, ml/min/1.73 m$^2$ | 1.00 | 0.99 to 1.00 | 0.114 | 0.99 | 0.99 to 1.00 | 0.08 |
| Diabetes mellitus | 1.35 | 1.07 to 1.71 | 0.01 | 1.42 | 1.08 to 1.17 | 0.01 |
| ACEI or ARB treatment | 0.76 | 0.51 to 1.11 | 0.16 | 0.75 | 0.47 to 1.17 | 0.2 |
| β-blocker treatment | 0.64 | 0.45 to 0.89 | 0.009 | 0.53 | 0.35 to 0.78 | 0.001 |
| Sodium | 0.97 | 0.94 to 1.01 | 0.12 | 0.95 | 0.92 to 0.99 | 0.03 |
| Hemoglobin | 0.90 | 0.84 to 0.96 | 0.002 | 0.96 | 0.88 to 1.04 | 0.34 |
| NT-proBNP* | 1.11 | 0.94 to 1.31 | 0.21 | 1.19 | 0.97 to 1.45 | 0.09 |
| Hs-cTnT*# | 1.7 | 1.43 to 2.03 | <0.001 | 1.54 | 1.22 to 1.93 | <0.001 |
| ST2#† | 1.12 | 1.02 to 1.23 | 0.02 | 1.11 | 0.99 to 1.24 | 0.05 |
| Neprilysin* | 1.16 | 1.04 to 1.30 | 0.009 | 1.17 | 1.03 to 1.32 | 0.02 |

HR, 95% CI and p-value are those obtained in the last step containing the variable. Composit primary endpoint was defined as cardiovascular death or HF hospitalization.
*NT-proBNP, hs-cTnT and Neprilysin as log(NT-proBNP), log(hs-cTnT) and log (Neprilysin) per 1 SD; CI, confindence interval;
the quadratic term also included in the model due to the quadratic relationship of the independent variables with the dependent variable;
†per 10 ng/ml.
HR, hazard ratio; HF, heart failure; LVEF, left ventricular ejection fraction; NYHA, New York Heart Association; eGFR, estimated glomerular filtration rate (CKD-EPI); ACEI, angiotensin-converting enzyme inhibiter; ARB, angiotensin II receptor blocker; NT-proBNP, N-terminal pro-brain natriuretic peptide; Hs-cTnT = high sensitivity cardiac troponin T. ST2 = soluble ST2.

REFERENCES CITED IN THE APPLICATION

Bayes-Genis A, de Antonio M, Galan A, Sanz H, Urrutia A, Cabanes R, et al. Combined Use of High Sensitivity ST2 and NTproBNP to Improve the Prediction of Death in Heart Failure. Eur J Heart Fail 2012; 14:32-8.

---

The invention claimed is:

1. An in vitro method for determining the prognosis in a patient suffering a heart failure disease (HF), the method comprising the step of determining the level of soluble neprilysin (NEP) in a test sample of the patient.

2. The in vitro method according to claim 1, wherein when the level of soluble NEP is higher than a reference value this is indicative of bad prognosis.

3. The in vitro method according to claim 1, wherein the level of soluble NEP is determined by an immunoassay technique.

4. The in vitro method according to claim 3, wherein the immunoassay technique is a sandwich assay.

5. The in vitro method according to claim 4, wherein the sandwich assay is an ELISA.

6. The in vitro method according to claim 1, wherein the test sample is selected from the group consisting of blood, serum, plasma, urine, and cerebrospinal fluid.

7. The in vitro method according to claim 6, wherein the test sample is serum or plasma.

8. The in vitro method according to claim 2, wherein the bad prognosis is the risk of a cardiovascular event selected from the group consisting of: worsening or decompensation of heart failure, and mortality.

9. The in vitro method of claim 8, wherein the risk of the cardiovascular event proportionally increases with the level of soluble NEP.

10. The in vitro method according to claim 1, wherein the patient is suffering chronic HF.

11. The in vitro method according to claim 1, wherein the determination of the level of soluble NEP is performed by contacting the sample with an antibody or a fragment thereof which specifically binds to soluble NEP.

12. The in vitro method of claim 11, wherein the antibody or fragment thereof, forms part of a kit.

13. A method of deciding or recommending to initiate a medical regimen based on NEP inhibitors in a subject suffering a heart failure disease, which method comprises the steps of (a) determining, in vitro, the amount of soluble NEP in a test sample of the subject; and (b) comparing the amount obtained in step (a) with a reference value, wherein if the amount of soluble NEP detected in step (a) is higher than the reference value it is indicative that the subject would benefit from a medical regimen based on NEP inhibitors.

* * * * *

SEQUENCE LISTING

<160> NUMBER OF SEQ ID NOS: 1

<210> SEQ ID NO 1
<211> LENGTH: 698
<212> TYPE: PRT
<213> ORGANISM: Homo sapiens

<400> SEQUENCE: 1

```
Asp Asp Gly Ile Cys Lys Ser Ser Asp Cys Ile Lys Ser Ala Ala Arg
1               5                   10                  15

Leu Ile Gln Asn Met Asp Ala Thr Thr Glu Pro Cys Thr Asp Phe Phe
            20                  25                  30

Lys Tyr Ala Cys Gly Gly Trp Leu Lys Arg Asn Val Ile Pro Glu Thr
        35                  40                  45

Ser Ser Arg Tyr Gly Asn Phe Asp Ile Leu Arg Asp Glu Leu Glu Val
    50                  55                  60

Val Leu Lys Asp Val Leu Gln Glu Pro Lys Thr Glu Asp Ile Val Ala
65                  70                  75                  80

Val Gln Lys Ala Lys Ala Leu Tyr Arg Ser Cys Ile Asn Glu Ser Ala
            85                  90                  95

Ile Asp Ser Arg Gly Gly Glu Pro Leu Leu Lys Leu Leu Pro Asp Ile
            100                 105                 110

Tyr Gly Trp Pro Val Ala Thr Glu Asn Trp Glu Gln Lys Tyr Gly Ala
        115                 120                 125
```

```
Ser Trp Thr Ala Glu Lys Ala Ile Ala Gln Leu Asn Ser Lys Tyr Gly
    130                 135                 140
Lys Lys Val Leu Ile Asn Leu Phe Val Gly Thr Asp Lys Asn Ser
145                 150                 155                 160
Val Asn His Val Ile His Ile Asp Gln Pro Arg Leu Gly Leu Pro Ser
                    165                 170                 175
Arg Asp Tyr Tyr Glu Cys Thr Gly Ile Tyr Lys Glu Ala Cys Thr Ala
                180                 185                 190
Tyr Val Asp Phe Met Ile Ser Val Ala Arg Leu Ile Arg Gln Glu Glu
                195                 200                 205
Arg Leu Pro Ile Asp Glu Asn Gln Leu Ala Leu Glu Met Asn Lys Val
    210                 215                 220
Met Glu Leu Glu Lys Glu Ile Ala Asn Ala Thr Ala Lys Pro Glu Asp
225                 230                 235                 240
Arg Asn Asp Pro Met Leu Leu Tyr Asn Lys Met Thr Leu Ala Gln Ile
                245                 250                 255
Gln Asn Asn Phe Ser Leu Glu Ile Asn Gly Lys Pro Phe Ser Trp Leu
                260                 265                 270
Asn Phe Thr Asn Glu Ile Met Ser Thr Val Asn Ile Ser Ile Thr Asn
    275                 280                 285
Glu Glu Asp Val Val Val Tyr Ala Pro Glu Tyr Leu Thr Lys Leu Lys
    290                 295                 300
Pro Ile Leu Thr Lys Tyr Ser Ala Arg Asp Leu Gln Asn Leu Met Ser
305                 310                 315                 320
Trp Arg Phe Ile Met Asp Leu Val Ser Ser Leu Ser Arg Thr Tyr Lys
                325                 330                 335
Glu Ser Arg Asn Ala Phe Arg Lys Ala Leu Tyr Gly Thr Thr Ser Glu
                340                 345                 350
Thr Ala Thr Trp Arg Arg Cys Ala Asn Tyr Val Asn Gly Asn Met Glu
    355                 360                 365
Asn Ala Val Gly Arg Leu Tyr Val Glu Ala Ala Phe Ala Gly Glu Ser
    370                 375                 380
Lys His Val Val Glu Asp Leu Ile Ala Gln Ile Arg Glu Val Phe Ile
385                 390                 395                 400
Gln Thr Leu Asp Asp Leu Thr Trp Met Asp Ala Glu Thr Lys Lys Arg
                405                 410                 415
Ala Glu Glu Lys Ala Leu Ala Ile Lys Glu Arg Ile Gly Tyr Pro Asp
                420                 425                 430
Asp Ile Val Ser Asn Asp Asn Lys Leu Asn Asn Glu Tyr Leu Glu Leu
    435                 440                 445
Asn Tyr Lys Glu Asp Glu Tyr Phe Glu Asn Ile Ile Gln Asn Leu Lys
    450                 455                 460
Phe Ser Gln Ser Lys Gln Leu Lys Lys Leu Arg Glu Lys Val Asp Lys
465                 470                 475                 480
Asp Glu Trp Ile Ser Gly Ala Ala Val Val Asn Ala Phe Tyr Ser Ser
                485                 490                 495
Gly Arg Asn Gln Ile Val Phe Pro Ala Gly Ile Leu Gln Pro Pro Phe
                500                 505                 510
Phe Ser Ala Gln Gln Ser Asn Ser Leu Asn Tyr Gly Gly Ile Gly Met
    515                 520                 525
Val Ile Gly His Glu Ile Thr His Gly Phe Asp Asp Asn Gly Arg Asn
    530                 535                 540
Phe Asn Lys Asp Gly Asp Leu Val Asp Trp Trp Thr Gln Gln Ser Ala
```

```
                     545                 550                 555                 560
Ser Asn Phe Lys Glu Gln Ser Gln Cys Met Val Tyr Gln Tyr Gly Asn
                565                 570                 575

Phe Ser Trp Asp Leu Ala Gly Gly Gln His Leu Asn Gly Ile Asn Thr
                580                 585                 590

Leu Gly Glu Asn Ile Ala Asp Asn Gly Gly Leu Gly Gln Ala Tyr Arg
                595                 600                 605

Ala Tyr Gln Asn Tyr Ile Lys Lys Asn Gly Glu Glu Lys Leu Leu Pro
            610                 615                 620

Gly Leu Asp Leu Asn His Lys Gln Leu Phe Phe Leu Asn Phe Ala Gln
625                 630                 635                 640

Val Trp Cys Gly Thr Tyr Arg Pro Glu Tyr Ala Val Asn Ser Ile Lys
                645                 650                 655

Thr Asp Val His Ser Pro Gly Asn Phe Arg Ile Ile Gly Thr Leu Gln
                660                 665                 670

Asn Ser Ala Glu Phe Ser Glu Ala Phe His Cys Arg Lys Asn Ser Tyr
                675                 680                 685

Met Asn Pro Glu Lys Lys Cys Arg Val Trp
            690                 695
```